United States Patent [19]

Decarie et al.

[11] Patent Number: 5,611,780
[45] Date of Patent: Mar. 18, 1997

[54] ENDOSCOPIC SURGICAL METHOD

[75] Inventors: Andre P. Decarie, Royersford, Pa.; David L. Brown, Wallingford, Conn.; Stanley J. Malinowski, Guilford, Conn.; Douglas M. Dunklee, Bridgeport, Conn.

[73] Assignee: United States Surgical Corporation, Norwalk, Conn.

[21] Appl. No.: 241,167

[22] Filed: May 10, 1994

Related U.S. Application Data

[63] Continuation of Ser. No. 916,368, Jul. 20, 1992, Pat. No. 5,315,985, which is a continuation of Ser. No. 673,233, Mar. 21, 1991, Pat. No. 5,144,942.

[51] Int. Cl.$^6$ .................................................... A61M 5/178
[52] U.S. Cl. ............................................................ 604/164
[58] Field of Search ...................................... 604/264, 164

[56] References Cited

U.S. PATENT DOCUMENTS

| | | |
|---|---|---|
| 2,219,605 | 10/1940 | Turkel ........................................ 604/164 |
| 3,013,656 | 12/1961 | Murphy, Jr. . |
| 3,061,087 | 10/1962 | Scrivens et al. . |
| 3,241,554 | 3/1966 | Coanda . |
| 3,613,685 | 10/1969 | Reynolds . |
| 3,770,119 | 11/1973 | Hultberg et al. . |
| 3,954,174 | 5/1976 | Kraus . |
| 4,128,173 | 12/1978 | Lazarus et al. . |
| 4,195,734 | 4/1980 | Boner et al. . |
| 4,212,304 | 7/1980 | Finney ........................................ 206/471 |
| 4,262,800 | 4/1981 | Nethercutt . |
| 4,355,018 | 10/1982 | Hansen et al. . |
| 4,420,461 | 12/1983 | Recket et al. . |
| 4,426,357 | 1/1984 | Buffington et al. . |
| 4,436,824 | 3/1984 | Bishop . |
| 4,479,792 | 10/1984 | Lazarus et al. . |
| 4,482,053 | 11/1984 | Alpern et al. . |
| 4,499,183 | 2/1985 | Sujansky et al. . |
| 4,501,363 | 2/1985 | Isbey, Jr. . |
| 4,523,679 | 6/1985 | Paikoff et al. . |
| 4,535,773 | 8/1985 | Yoon . |
| 4,573,576 | 3/1986 | Krol ........................................... 206/471 |
| 4,589,415 | 5/1986 | Haaga ......................................... 604/164 |
| 4,601,710 | 7/1986 | Moll . |
| 4,654,030 | 3/1987 | Moll et al. . |
| 4,784,137 | 11/1988 | Kulik et al. . |
| 4,808,168 | 2/1989 | Warring . |
| 4,813,929 | 3/1989 | Semrad . |
| 4,989,733 | 2/1991 | Patry . |
| 5,040,715 | 8/1991 | Green et al. . |
| 5,071,410 | 12/1991 | Pazell ........................................ 604/164 |
| 5,074,867 | 12/1991 | Wilk .......................................... 604/264 |
| 5,084,057 | 1/1992 | Green et al. . |
| 5,112,310 | 5/1992 | Grobe ........................................ 604/175 |
| 5,158,543 | 10/1992 | Lazarus ...................................... 604/164 |

FOREIGN PATENT DOCUMENTS

| | | |
|---|---|---|
| 1192525 | 8/1985 | Canada . |
| 0113520 | 7/1984 | European Pat. Off. . |
| 0232600 | 8/1987 | European Pat. Off. . |
| 0399701 | 11/1990 | European Pat. Off. . |
| 0409569 | 1/1991 | European Pat. Off. . |

OTHER PUBLICATIONS

E–Pack Procedure Kit, Jan. 1988.
Concept Universal Cannula Kit, Concept Incorporated, May 1, 1989.
Concept, Inc., "Zone Specific Cannula Set", May 1, 1988.
Richard Wolf Medical Instruments Corp., "Laparoscopy Price List", Jan. 1, 1988.
R. Wolf Endoscopes, "OB–GYN Price List", Nov. 15, 1980.
Olympus 1988 Price List.

*Primary Examiner*—Todd E. Manahan

[57] ABSTRACT

The present disclosure relates to a method of performing endoscopic or laparoscopic surgical procedures, including the steps of providing an endoscopic kit including an obturator for penetrating body tissue and at least two sleeve members adapted for use with the obturator. The method further includes the steps of inserting the obturator into a first sleeve member, penetrating a body wall of a patient with the obturator and the first sleeve member, and removing the obturator from the first sleeve member such that the first sleeve member remains in the body wall. The method further includes the steps of inserting the obturator into a second sleeve member, penetrating the body wall with the obturator and the second sleeve member, and removing the obturator from the second sleeve member such that the second sleeve member remains in the body wall.

4 Claims, 6 Drawing Sheets

ENDOSCOPIC SURGICAL METHOD

CROSS-REFERENCE TO RELATED APPLICATIONS

This application is a continuation application of Ser. No. 07/916,368 filed Jul. 20, 1992, now U.S. Pat. No. 5,315,985 which was a continuation application of U.S. application Ser. No. 07/673,233, filed Mar. 21, 1991 now U.S. Pat. No. 5,144,942.

BACKGROUND OF THE INVENTION

1. Field of the Invention

The present invention relates to endoscopic and laparoscopic surgical instruments, and more particularly to a kit for packaging endoscopic or laparoscopic surgical instruments for use during a surgical procedure.

2. Discussion of the Prior Art

Endoscopic and laparoscopic surgical procedures have increased in popularity in recent years. Such surgical procedures provide an attractive alternative to major surgery involving large incisions in the patient which leaves considerable scarring and extensive recovery periods. Laparoscopic and endoscopic surgical procedures utilize small incisions with minimal damage to tissue in the areas surrounding the surgical objective. By minimizing the trauma to surrounding tissue, laparoscopic and endoscopic surgical procedures significantly reduce the recovery time and lessen the amount of scar tissue at the incision.

Laparoscopic and endoscopic surgery generally requires the use of instruments or equipment which provides a passage through the skin and surrounding tissue to the surgical site. Typically, a trocar assembly is used in which a sharp, pointed obturator is used to puncture and penetrate the skin and surrounding tissue to reach the surgical area. The obturator is positioned within a sleeve member which remains in place after the obturator has been removed. The sleeve member provides a path for the insertion of the surgical equipment, which generally may include a viewing device as well as a cutting instrument, laser instrument, grippers, dissectors or the like. In practice, often times many trocar and sleeve members are used to provide for the use of numerous surgical instruments to carry out the surgical procedure.

In view of this, it is required that assistants to the surgical procedure prepare for the operation by making ready numerous trocar assemblies and other instruments to aid in the performance of the surgical procedure. To this end, the individual packaging of each of these devices leads to the accumulation of packaging material within the sterile environment of the operating room. It is also conceivable that certain necessary pieces of operating equipment and instrumentation will be inadvertently omitted from the operating room, thus delaying the surgical procedure or inconveniencing the surgeon and jeopardizing the safety of the patient. Furthermore, the cost of the equipment becomes a factor, as each trocar assembly includes an obturator and a trocar sleeve, thus requiring the purchase of numerous trocar assemblies although conceivably only one obturator will be used.

The novel endoscopic instrumentation kit of the present invention obviates the disadvantages encountered in the prior art and provides an endoscopic or laparoscopic instrumentation kit which may include all the necessary pieces of equipment required for laparoscopic and endoscopic surgical procedures. The amount of packaging material which must be discarded is significantly reduced, and the possibility of the omission of a required piece of equipment is essentially eliminated.

SUMMARY OF THE INVENTION

The present invention provides a novel endoscopic or laparoscopic instrumentation kit which makes available, in various combinations, the necessary equipment for effecting a laparoscopic surgical procedure. The requirement for numerous packages of individual pieces of equipment is eliminated, as is the associated need for disposal of the individual packaging material in the operating room. The inadvertent omission of critical pieces of equipment or instrumentation is significantly reduced or eliminated, thus increasing the efficiency of the surgical procedure and insuring the safety of the patient. In addition, cost is reduced, since the need to purchase numerous trocar assemblies, which each include an obturator and a trocar sleeve, is eliminated. A single obturator may be purchased with a plurality of trocar sleeves, thus reducing the cost of equipment for an operation.

The present invention also provides a novel package for endoscopic or laparoscopic instrumentation, which retains and displays the laparoscopic or endoscopic instrumentation provided for in the kit of the present invention.

The endoscopic instrumentation kit of the present invention essentially comprises at least one trocar assembly which includes at least one obturator and at least one more sleeve member than each obturator provided. The obturator is insertable into the sleeve members during the surgical procedure. Each obturator and sleeve member is packaged in an enclosure so that the instrumentation may be viewed by the surgical staff prior to removal from the packaging. Preferably, at least two sleeve members are provided per obturator.

The endoscopic instrumentation kit may further include a catheter device, as well as other necessary surgical equipment to enable the surgical staff to carry out the endoscopic or laparoscopic procedure. The additional equipment may include a surgical operating instrument such as a cutting device, a stapling or clip applying device, a dissector, or a gripping device. These instruments generally include an elongated shaft having a handle mechanism at one end and the operative mechanism at the other end. During the surgical procedure, the instrument is insertable through the sleeve member which remains in the patient's body after removal of the obturator. Also contemplated for inclusion in the kit are tissue-gripping sleeve members which secure a sleeve member in a patient, as well as attachment devices for the trocar sleeves which modify the inner diameter of the sleeve at the end of the sleeve which is outside the patient's body to maintain a gas seal between the instrument which is inserted into the trocar sleeve and the attachment device.

The instrumentation kit of the present invention may be packaged as a single sterile package in which all the instruments are provided in a single vacuum-formed plastic retainer which comprises the top cover of the package, along with a flat rigid bottom cover which is generally comprised of spun-bonded plastic fibers such as polyolefin, and is preferably Tyvek (a registered trademark of Dupont), or other rigid material such as plastic or cardboard. Tyvek is a preferred material for the bottom cover, since the package may be sterilized after the instruments are sealed within through the Tyvek, according to known sterilizing procedures. The vacuum-formed top cover provides recesses which correspond in shape and dimensions to the individual instruments packaged therein, which serves to retain the individual instruments while displaying them for the surgical staff. Alternately, two distinct compartments may be provided, for packaging in a first compartment the obturator, trocar sleeve members, and a catheter and/or pneumoperitoneum needle, if provided. The second compartment is provided to package the surgical instrument, tissue-gripping sleeves, and adaptor members for the sleeve members of the trocar assembly. The two compartments may be joined so that they are separable along a tear line or separation line, or they may be separate but packaged together in a final shipping carton. Preferably, the compartments may be pivoted along the tear line into a stacked configuration for final packaging and shipping.

BRIEF DESCRIPTION OF THE DRAWINGS

The foregoing features of the present invention will become more readily apparent and may be understood by referring to the following detailed description of an illustrative embodiment of the endoscopic or laparoscopic surgical instrumentation kit and its novel packaging device, taken in conjunction with the accompanying drawings, in which.

DETAILED DESCRIPTION OF THE PREFERRED EMBODIMENTS

Figure 1:
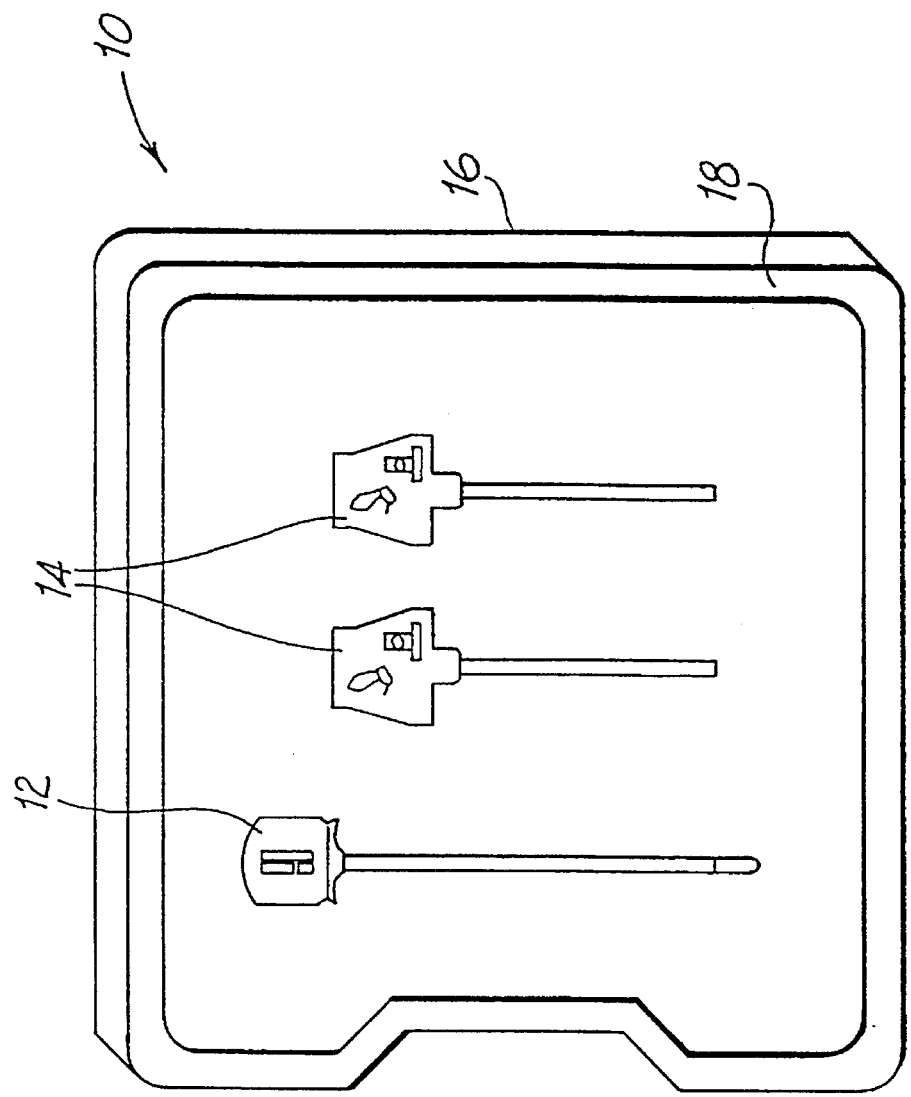
FIG. 1 illustrates a top plan view of the preferred embodiment of the endoscopic instrumentation kit of the present invention.

Referring now in specific detail to the drawings, in which like reference numerals identify similar or identical elements throughout the several views, FIG. 1 shows the endoscopic instrumentation kit 10 of the present invention. The preferred embodiment of kit 10 includes a trocar device which comprises obturator 12 and trocar sleeve members 14. At least one more sleeve member 14 is provided for each obturator 12 provided in the kit, preferably in a ratio of two sleeve members per each obturator provided, so that numerous surgical ports may be created during the surgical procedure. Obturator 12 and sleeves 14 are packaged in kit 10, and the package essentially comprises a bottom cover 16 of a flat rigid material such as Tyvek, which provides for sterilization after packaging, and a vacuum-formed top plastic cover 18 which encloses and displays obturator 12 and sleeves 14. Top cover 18 is preferably transparent to provide an unobstructed view of the instrumentation packaged therein.

It is contemplated that the kit provide only one obturator for a given size, and include several obturators, each of a different size. At least one additional sleeve member is then provided in relation to the number of obturators, but preferably in a ratio of two sleeves per each obturator provided.

Figure 2:
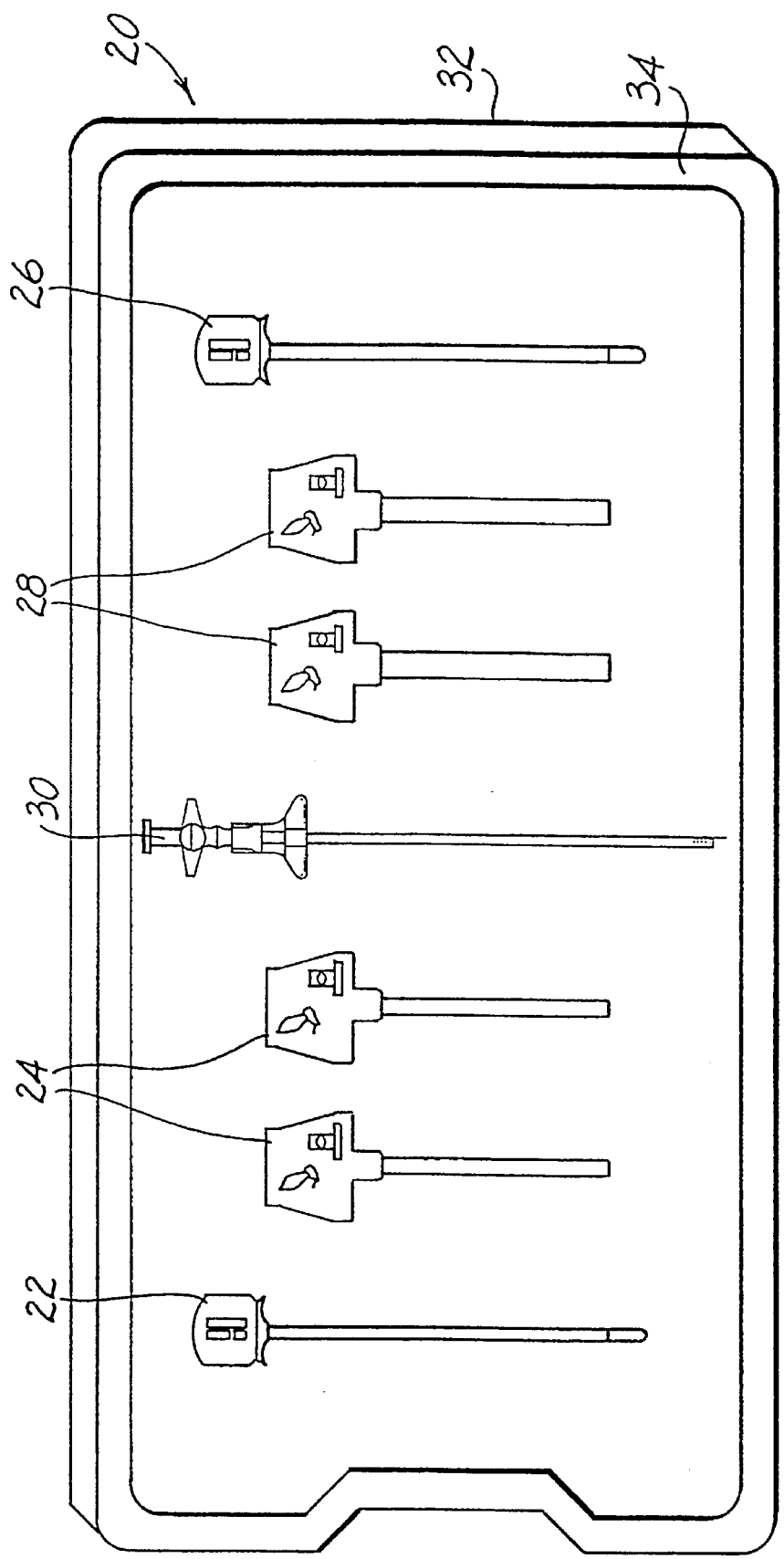
FIG. 2 illustrates a top plan view of an alternate embodiment of the kit of the present invention.

FIG. 2 illustrates an alternate embodiment of the kit of FIG. 1. Kit 20 comprises a pair of trocar assemblies, which includes obturator 22 and its associated trocar sleeve members 24, as well as obturator 26 and its sleeve members 28. Preferably, obturator 22 and obturator 26 are of different diameters, to provide different incision or puncture holes in the patient's body. Sleeve members 24 and 28 are of a diameter to accept their associated obturators, and provide different sized openings to accept various pieces of surgical equipment. Also provided in kit 20 is a pneumoperitoneum needle 30 whose use is conventional in surgical procedures. A catheter may also be provided if desired. Kit 20 is packaged with a rigid bottom cover 32 and a vacuum-formed transparent plastic cover 34 which is provided with raised wall portions corresponding in size to the instrumentation packaged therein for retaining and displaying the surgical instruments.

Figure 3:
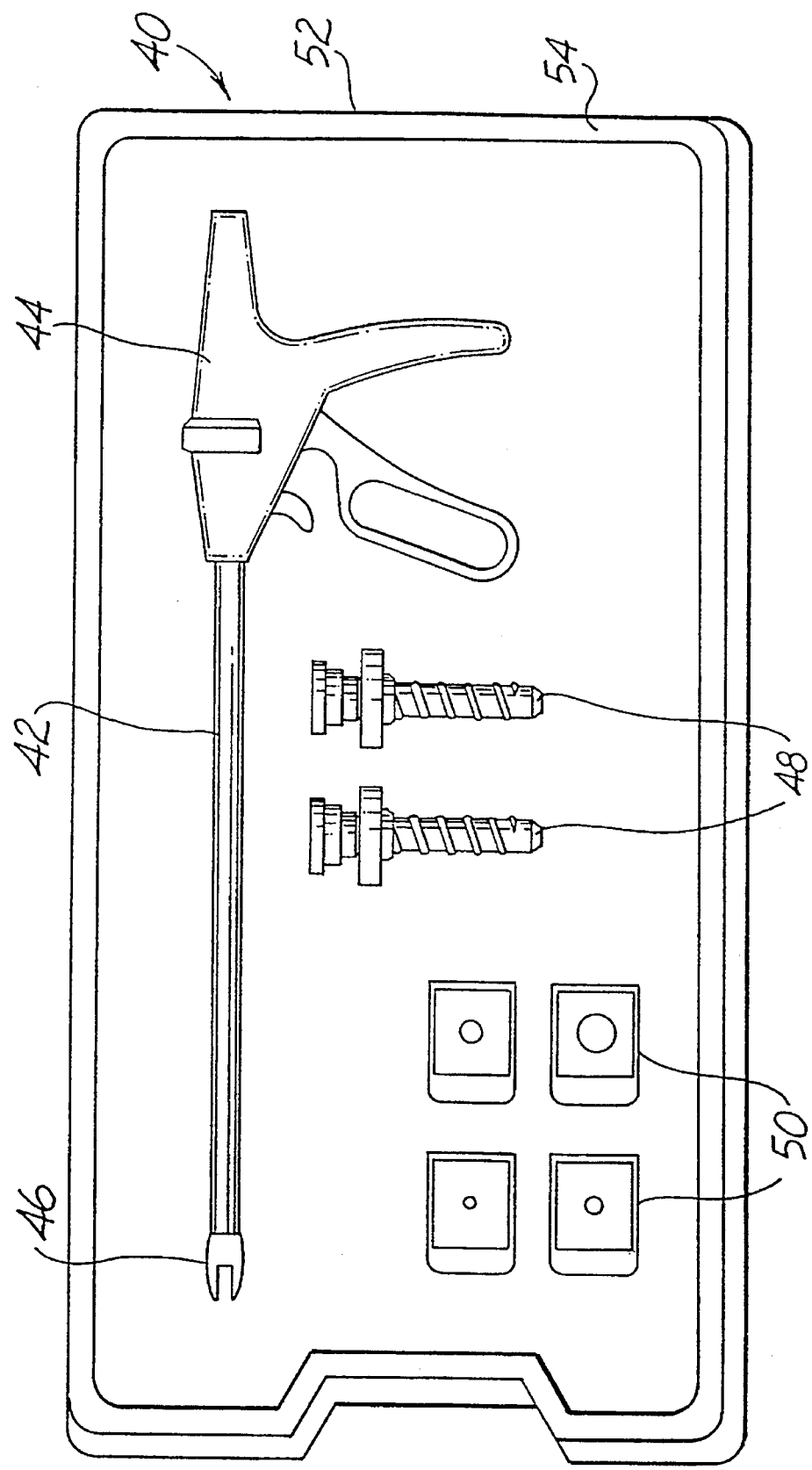
FIG. 3 illustrates a top plan view of a further alternate embodiment of the kit of the present invention.

FIG. 3 illustrates a further embodiment of the kit of the present invention which provides the operating equipment for the laparoscopic or endoscopic surgical procedure. Kit 40 provides an endoscopic surgical instrument 42 which comprises an elongated shaft having a handle mechanism 44 at one end and an operative mechanism 46 at a second end. Mechanism 46 generally comprises a clip mechanism for applying surgical staples or clips at the surgical site. Instrument 42 is dimensioned to be insertable through trocar sleeve members 14, 24 or 28 after the obturator has been removed. Also included in kit 40 are tissue-gripping sleeve members 48 which are provided with threads for allowing the rotatable insertion of tissue-gripping sleeves 48 into an incision in the patient's body with trocar sleeve members 14, 24 and 28 to secure the sleeve members in the patient. Tissue-gripping sleeve members 48 grip the tissue at the incision to reduce slippage during instrument manipulation during the surgical procedure. Kit 40 further includes attachment devices 50 for use with trocar sleeve members 14, 24 and 28 which modify the inner diameter of sleeve members 14, 24 and 28 to accommodate instruments of various sizes. Attachment devices 50 secure to an end of sleeve members 14, 24 and 28 outside the patient's body to provide a gas seal with instruments of corresponding diameters that are inserted into the sleeve members. Kit 40 includes bottom cover 52 which is similar to bottom covers 16 and 32 described above. Top cover 54 is constructed of vacuum formed transparent plastic having upstanding walls corresponding in shape to the instrumentation provided in kit 40 to retain and display the instruments while maintaining the sterility of the kit 40.

Figure 4:
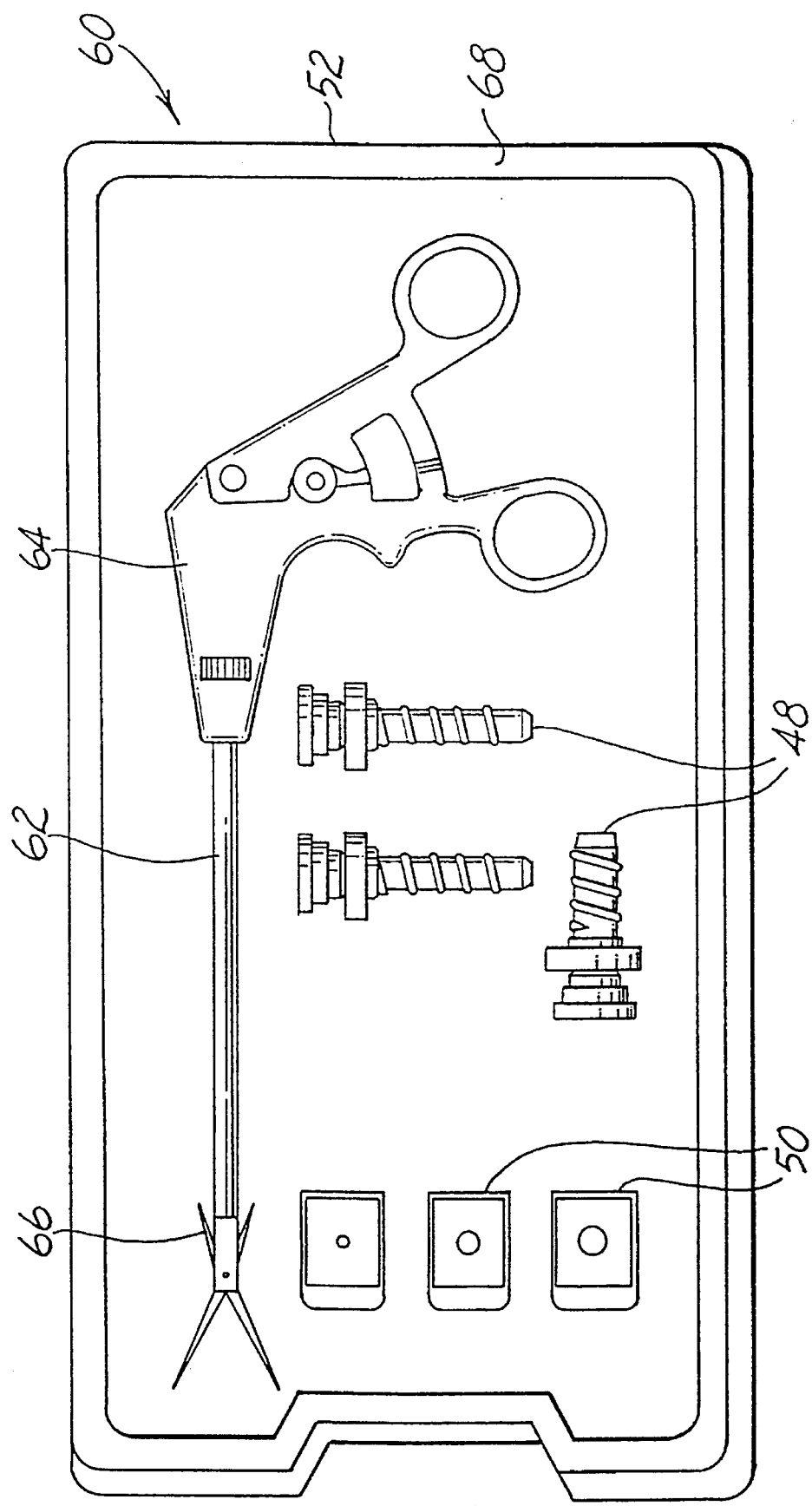
FIG. 4 illustrates a top plan view of an alternate embodiment of the kit of FIG. 3.

FIG. 4 illustrates a further kit 60 which is similar to kit 40 of FIG. 3 except for the provision of surgical instrument 62. Instrument 62 is provided with a handle member 64 and an operative mechanism 66, which generally comprises a cutting instrument, gripping instrument, dissecting instrument, or the like. Top cover 68 is provided having upstanding walls which correspond in shape to instrument 62 as well as gripping sleeves 48 and attachment devices 50 for retaining and displaying these instruments.

Figure 5:
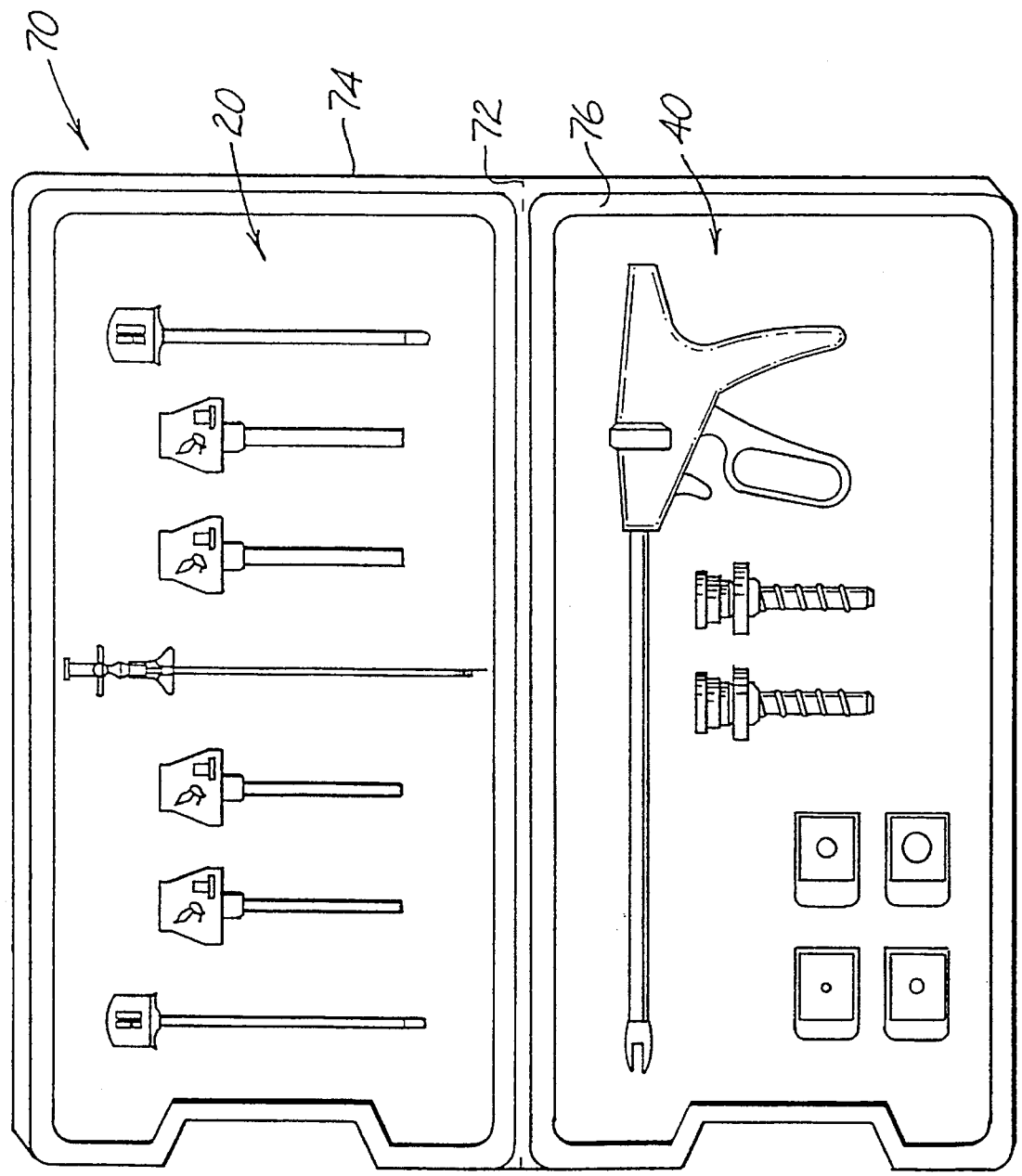
FIG. 5 illustrates a top plan view of a further embodiment of the kit of the present invention.

Turning now to FIG. 5, endoscopic instrumentation kit 70 is illustrated which shows kits 20 and 40 packaged together for use in a single operative procedure. Kit 70 essentially comprises kit 20 as shown in FIG. 2 and kit 40 as shown in FIG. 3 which are packaged together in a single container. A bottom cover 74, constructed preferably of Tyvek, is provided and is secured to a vacuum-formed top cover 76 which is provided with raised wall sections which correspond in shape to the instrumentation packaged therein to retain and display the equipment as shown. A separation line 72 may be provided, which consists of a scored line, perforations or the like. Separation line 72 allows the individual kits 20 and 40 to be pivoted to be further packaged in a shipping carton or wrap in a stacked configuration, and further allows kits 20 and 40 to be separated while still contained within their individual packages.

Figure 6:
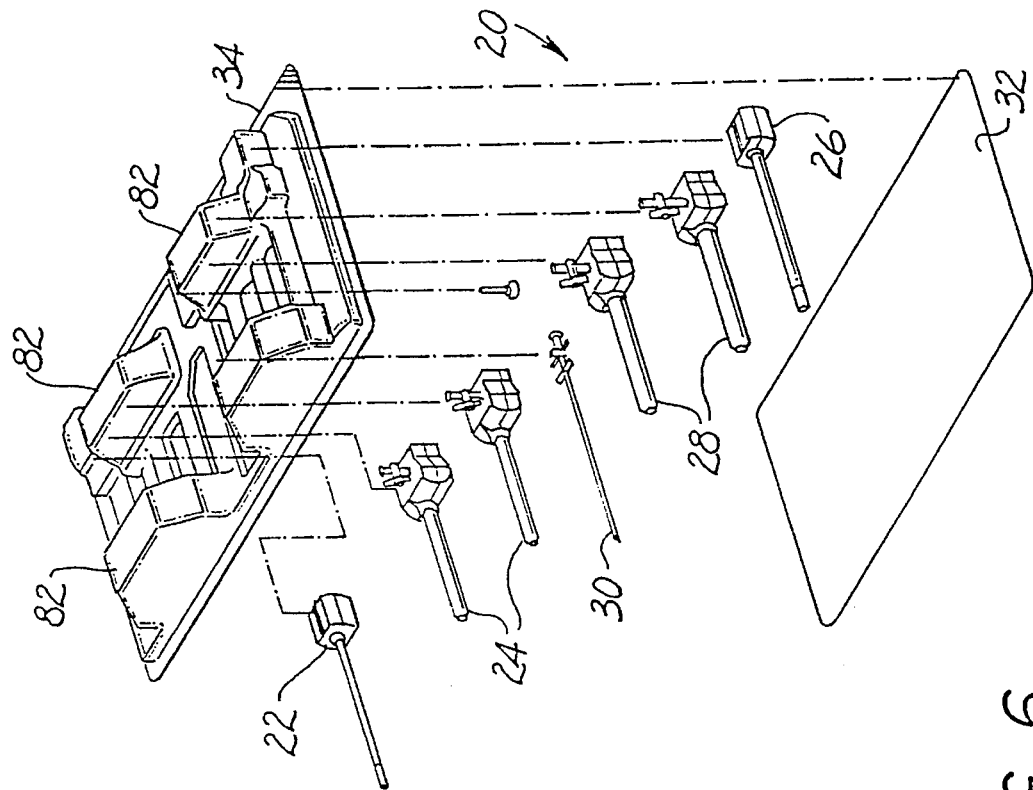
FIG. 6 illustrates the packaging device for the kit of the present invention.
Figure 6:
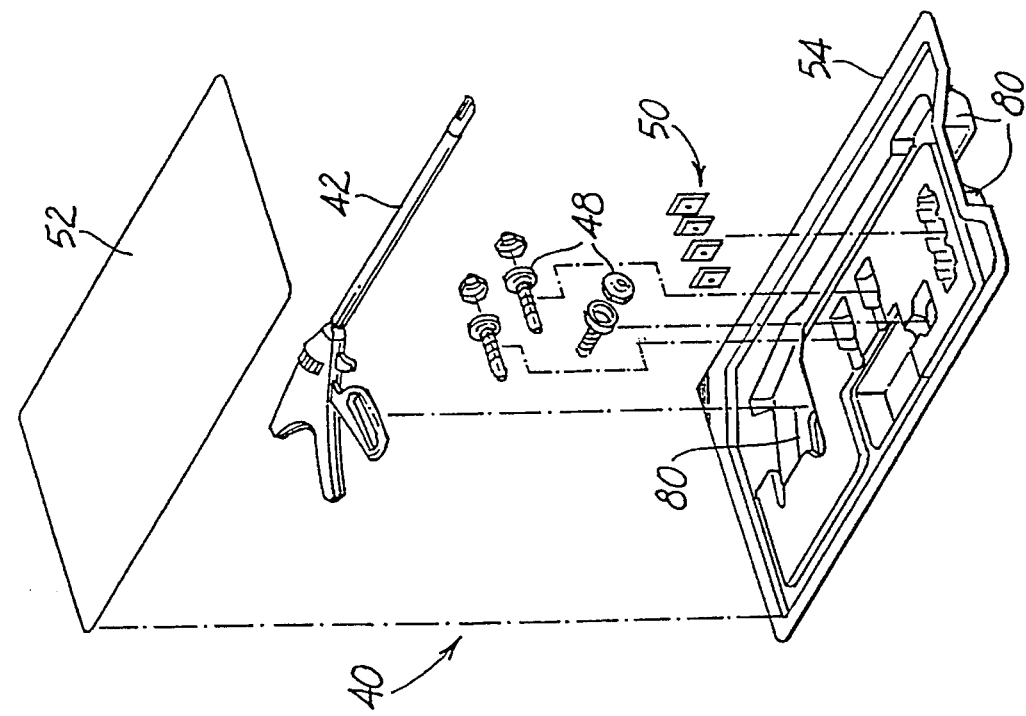

FIG. 6 illustrates the package containing the kits of the present invention. As seen in FIG. 6, individual kits 20 and 40 may be packaged separately and then stacked on each other to be further wrapped or enclosed in a separate box or wrap packaging material. Kit 40, as best described in relation to FIG. 3, comprises an endoscopic surgical instrument 42, tissue-gripping sleeves 48, and attachment devices 50, which are all packaged in top cover 54 with bottom cover 52 overlaying top cover 54. Top cover 54 is provided with raised wall members 80 which correspond in shape and dimensions to the instrumentation packaged therein to provide a means for retaining the instruments and displaying them to the surgical staff.

Kit 20, as best seen in FIG. 2, includes obturators 22 and 26 and their corresponding trocar sleeve members 24 and 28, as well as catheter 30. The instruments are assembled in top cover 34 and enclosed by bottom cover 32. Top cover 34 is provided with raised walls 82 which correspond in size and shape to the instruments packaged therein to provide means for retaining and displaying the instruments. Top covers 34 and 54 may be secured to bottom covers 32 and 52, respectively, by any conventional manner, including heat sealing, adhesives, or the like to ensure sterility of the final package.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A method of performing endoscopic or laparoscopic surgical procedures comprising the steps of:

providing an endoscopic kit including a first obturator for penetrating body tissue and first and second sleeve members adapted for use with the first obturator and a second obturator for penetrating body tissue and at least third and fourth sleeve members adapted for use with the second obturator, the third and fourth sleeve members being different in size than the first and second sleeve members;

inserting the first obturator into the first sleeve member;

penetrating a body wall of a patient with the first obturator and the first sleeve member;

removing the first obturator from the first sleeve member such that the first sleeve member remains in the body wall;

inserting the first obturator into the second sleeve member;

penetrating the body wall with the first obturator and the second sleeve member;

removing the obturator from the second sleeve member such that the second sleeve member remains in the body wall;

inserting the second obturator into the third sleeve member;

penetrating a body wall of a patient with the second obturator and the third sleeve member;

removing the second obturator from the third sleeve member such that the third sleeve member remains in the body wall;

inserting the second obturator into the fourth sleeve member;

penetrating the body wall with the second obturator and the fourth sleeve member; and removing the second obturator from the fourth sleeve member such that the fourth sleeve member remains in the body wall.

2. The method according to claim 1 wherein the steps of providing the first and second obturators comprise providing the first obturator in a size different from the size of the second obturator.

3. A method of performing endoscopic or laparoscopic surgical procedures comprising:

providing a package including a first trocar assembly having a first obturator disposed within a first sleeve member and at least a second sleeve member adapted for use with the first obturator and a second trocar assembly having a second obturator disposed within a third sleeve member and at least a fourth sleeve member adapted for use with the second obturator, the second obturator being of different size than the first obturator;

penetrating a body wall of a patient with the first trocar assembly;

removing the first obturator from the first sleeve member such that the first sleeve member remains in the body wall;

inserting the first obturator into the second sleeve member;

penetrating the body wall with the first obturator and the second sleeve member;

removing the first obturator from the second sleeve member such that the second sleeve member remains in the body wall;

penetrating a body wall of a patient with the second trocar assembly;

removing the second obturator from the third sleeve member such that the third sleeve member remains in the body wall;

inserting the second obturator into the fourth sleeve member;

penetrating the body wall with the second obturator and the fourth sleeve member;

removing the second obturator from the fourth sleeve member such that the fourth sleeve member remains in the body wall.

4. The method according to claim 3, wherein the step of providing the third and fourth sleeve members comprises providing the sleeves in a size different from the size of the first and second sleeve members.

* * * * *